United States Patent
Wolf et al.

(10) Patent No.: US 7,268,878 B2
(45) Date of Patent: Sep. 11, 2007

(54) FLUORESCENCE CORRELATION SPECTROSCOPY INSTRUMENT AND METHOD OF USING THE SAME

(75) Inventors: David E. Wolf, Sudbury, MA (US); Dylan A. Bulseco, Princeton, MA (US)

(73) Assignee: Sensor Technologies LLC, Shrewsbury, MA (US)

( * ) Notice: Subject to any disclaimer, the term of this patent is extended or adjusted under 35 U.S.C. 154(b) by 406 days.

(21) Appl. No.: 10/633,385

(22) Filed: Aug. 1, 2003

(65) Prior Publication Data

US 2004/0080750 A1   Apr. 29, 2004

Related U.S. Application Data

(60) Provisional application No. 60/461,394, filed on Apr. 8, 2003, provisional application No. 60/430,273, filed on Dec. 2, 2002, provisional application No. 60/400,503, filed on Aug. 1, 2002.

(51) Int. Cl.
*G01N 21/25* (2006.01)
(52) U.S. Cl. ..................................... 356/417
(58) Field of Classification Search ............... 356/417, 356/410, 416, 317, 318
See application file for complete search history.

(56) References Cited

U.S. PATENT DOCUMENTS

| | | | | |
|---|---|---|---|---|
| 5,220,172 A * | 6/1993 | Berthold et al. | ......... | 250/461.1 |
| 5,949,532 A * | 9/1999 | Schrof et al. | ................. | 356/73 |
| 6,200,818 B1 | 3/2001 | Eigen et al. | | |
| 6,203,994 B1 | 3/2001 | Epps et al. | | |
| 6,204,068 B1 * | 3/2001 | Soini et al. | ................. | 436/518 |
| 6,208,886 B1 * | 3/2001 | Alfano et al. | ............... | 600/473 |
| 6,579,690 B1 | 6/2003 | Bonnecaze et al. | | |
| 6,582,903 B1 | 6/2003 | Rigler et al. | | |
| 6,582,907 B1 | 6/2003 | Epps et al. | | |
| 6,589,730 B1 | 7/2003 | Larocca et al. | | |
| 6,603,546 B1 * | 8/2003 | Barbieri et al. | ............. | 356/318 |

FOREIGN PATENT DOCUMENTS

| | | |
|---|---|---|
| DE | 10035190 A1 | 2/2002 |
| EP | 0697 590 A1 | 2/1996 |
| EP | 697590 A1 | 2/1996 |
| WO | WO 03/006992 | 1/2003 |

OTHER PUBLICATIONS

Folds-Papp, Zeno et al., "Detection of single molecules: solution phase single-molecule fluorescence correlation spectroscopy as an ultrasensitive, rapid and reliable system for immunological investigation." *Journal of Immunological Methods*, 260 (2002) 117-124.

* cited by examiner

*Primary Examiner*—Roy M. Punnoose
(74) *Attorney, Agent, or Firm*—Allison Johnson

(57) ABSTRACT

Disclosed is a portable fluorescence correlation spectroscopy instrument that includes an excitation source, at least one of a light focusing element positioned to receive light emitted by the excitation source, a detector for detecting light, the detector positioned to receive light emitted by a sample excited by the excitation source, and a correlator coupled to the detector, the correlator for processing data received at the detector and providing data including autocorrelation data, crosscorrelation data, or a combination thereof.

66 Claims, 15 Drawing Sheets

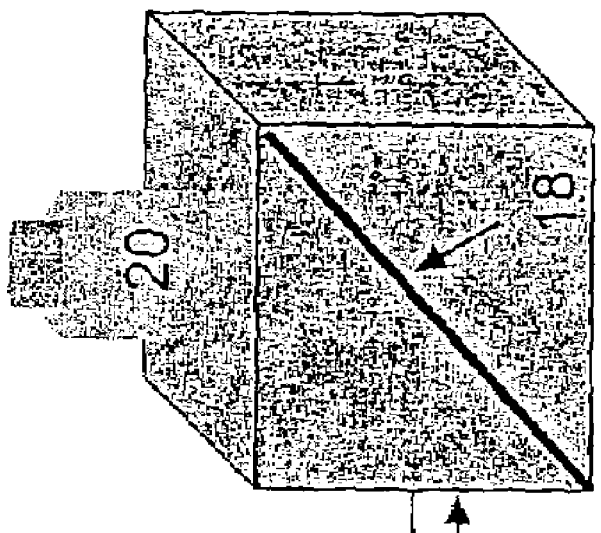
Fig. 3

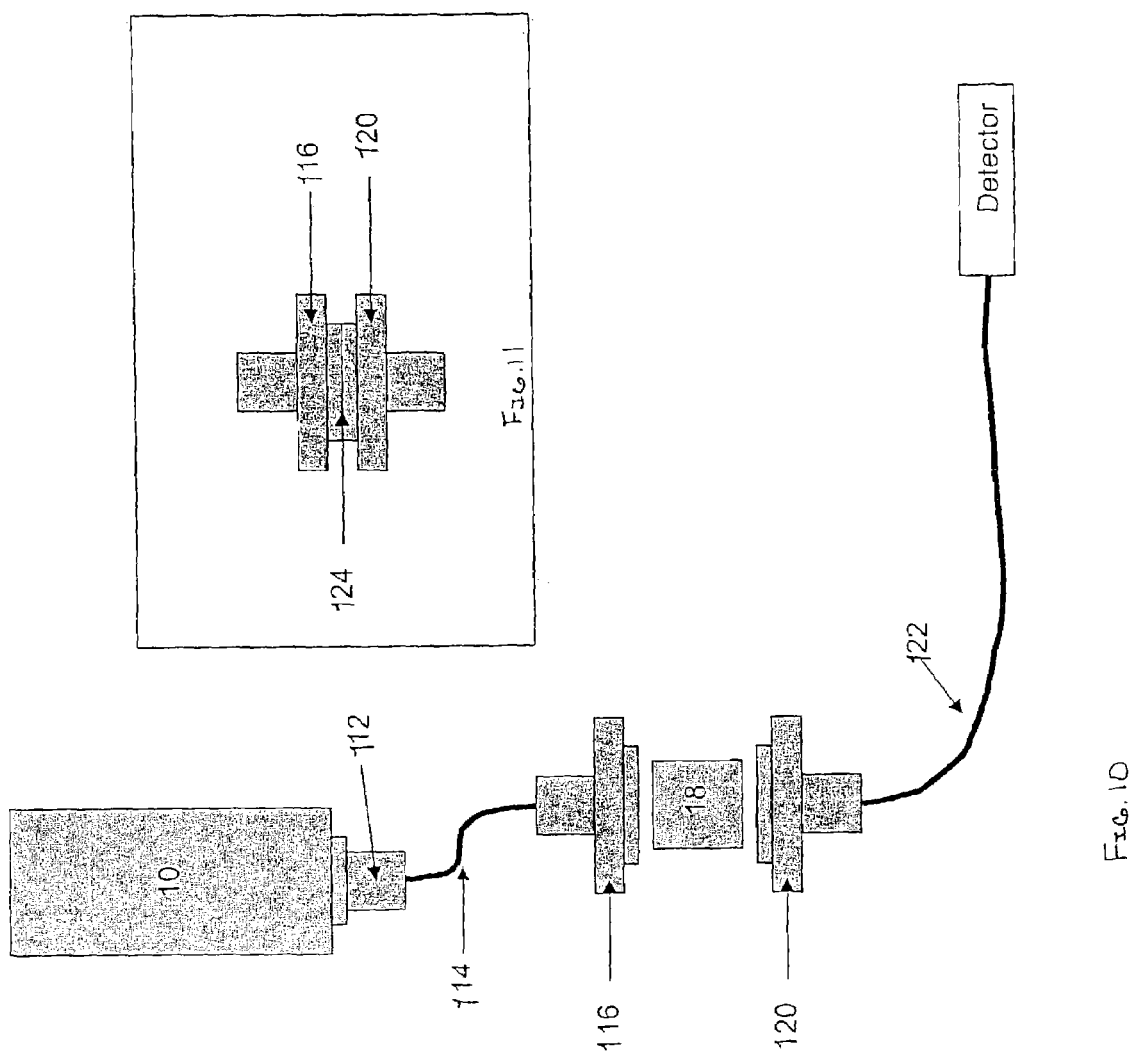

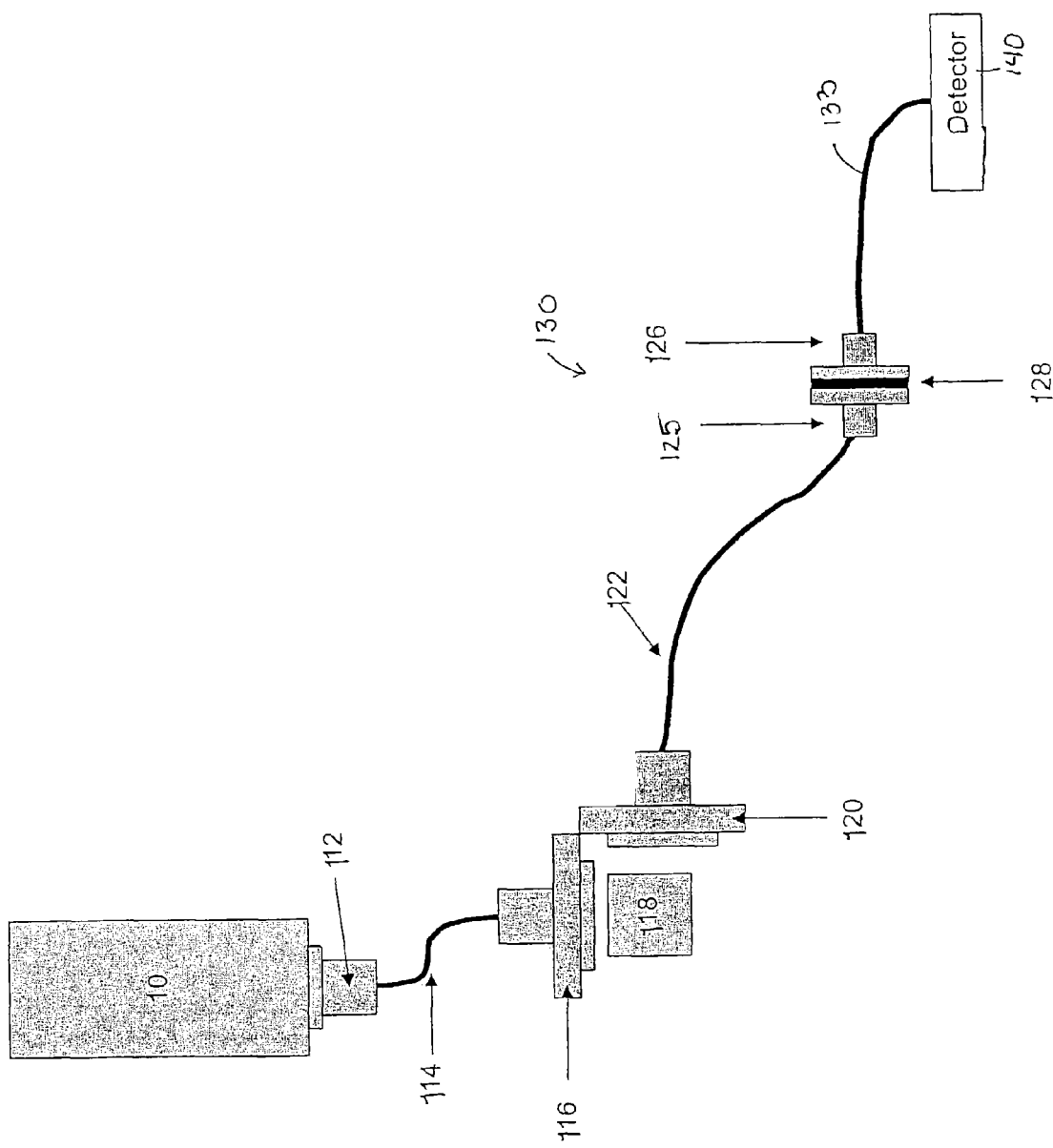

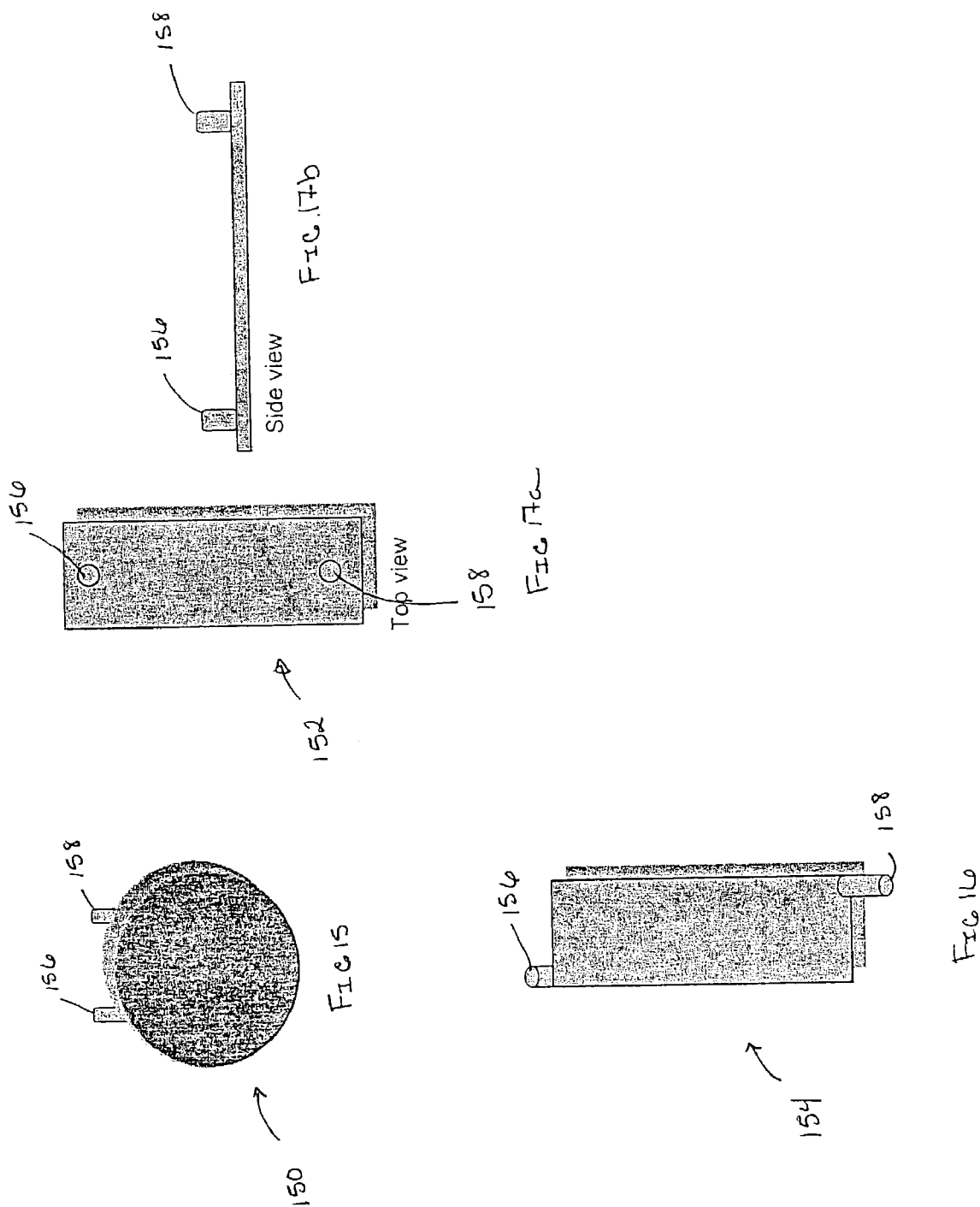

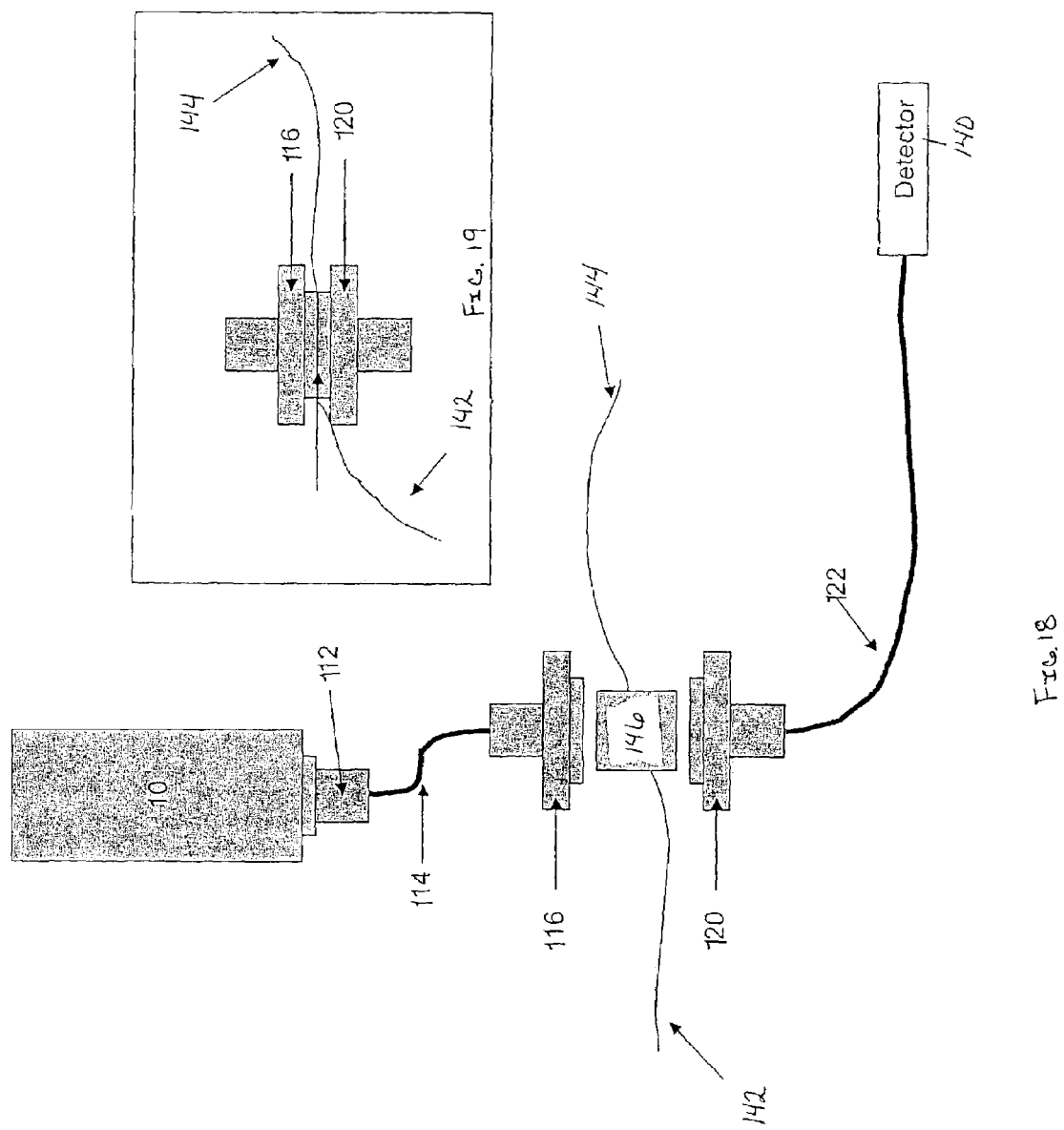

FLUORESCENCE CORRELATION SPECTROSCOPY INSTRUMENT AND METHOD OF USING THE SAME

CROSS REFERENCE TO RELATED APPLICATIONS

This application claims priority to U.S. Provisional Application Ser. No. 60/461,394, filed Apr. 8, 2003, U.S. Provisional Application Ser. No. 60/430,273 filed Dec. 2, 2002 and U.S. Provisional Application Ser. No. 60/400,503 filed Aug. 1, 2002.

BACKGROUND

The invention relates to fluorescence correlation spectroscopy.

Fluorescence correlation spectroscopy (FCS) is a single molecule detection method that has been used to detect molecules in small volume samples, e.g., femtoliters. FCS is a technique that employs confocal optics to limit the volume of sample studied to that of a confocal plane. The confocal plane is defined by the optical components of the system. FIG. 1 illustrates a laser beam illuminated volume of sample. A box is shown superimposed on the waist of the laser beam. The optical components of the system function to position the confocal plane in the waist of the laser beam. The diffusion of fluorescently labeled particles into and out of the illuminated confocal volume generates data related to fluorescence intensity fluctuation. Information about the particles in the sample can be extracted from this data.

Optics are employed in FCS to reduce out-of-focus light and limit image detection to the desired focal plane of in-focus light (i.e., the sample plane, which is also referred to as the image plane). The excitation volume (i.e., confocal volume) is minimized by illuminating the volume with a laser beam that has been focused to the limit of the resolution of a high numerical aperture objective lens. Out-of-focus light is eliminated by placing a field pinhole (i.e., aperture) in a conjugate image plane of the objective lens and before the detector. Eliminating out-of-focus light limits the volume of detection to the plane in which the object is focused. Signals from planes either above or below the object plane are focused either above or below the conjugate image plane, which renders them inefficiently collected due to the location of the aperture through which the focused image is allowed to pass. Fluorescently labeled particles that are in the sample of interest are detected only when the particles are present at the image plane of the confocal volume.

FCS is a technique used in biophysics, biochemistry, and cell biology. FCS can be used to study events at the level of single molecules. The diffusion times and the interaction of macromolecules, the absolute concentration of fluorescently labeled particles and the kinetics of chemical reactions can be measured using FCS. Applications of FCS have included studies related to ligand-receptor binding, protein-protein and protein-DNA interactions, and the aggregation of fluorescently labeled particles. The theory and applications of FCS are described in various references including Rigler, R. (1995), "Fluorescence correlations, single molecule detection and large number screening. Applications in biotechnology," J Biotechnol 41(2-3): 177-86; Schwille, P. (2001), "Fluorescence correlation spectroscopy and its potential for intracellular applications." Cell Biochem Biophys 34(3): 383-408; and Hess, S. T., S. Huang, et al. (2002). "Biological and chemical applications of fluorescence correlation spectroscopy: a review," Biochemistry 41(3): 697-705.

Typical FCS instruments are configured to include an epifluorescence microscope or a confocal microscope. These configurations are relatively large and require a user to focus and adjust the microscope and align the various components of the instrument prior to use.

SUMMARY

In one aspect, the invention features a portable fluorescence correlation spectroscopy instrument that includes an excitation source, at least one of a light focusing element (e.g., a lens, a fiber optic or a combination thereof) positioned to receive light emitted by the excitation source, a detector for detecting light, the detector positioned to receive light emitted by a sample excited by the excitation source, and a correlator coupled to the detector, the correlator for processing data received at the detector and providing data that includes autocorrelation data, crosscorrelation data, or a combination thereof. In one embodiment, the instrument further includes an emission filter positioned to transmit light to the detector, the emission filter adapted to transmit light having a wavelength greater than the wavelength of light emitted by the excitation source. In other embodiments, the light focusing element includes a fiber optic. In some embodiments, the fiber optic is coupled to the excitation source. In other embodiments, the instrument further includes an aperture positioned to receive light emitted by a sample excited by the excitation source. In one embodiment, the light focusing element includes a focusing lens.

In other embodiments, the instrument further includes a second light focusing element positioned to focus light emitted by the excitation source in a sample volume. In some embodiments, the instrument further includes a fiber optic coupled to the excitation source and the first light focusing element.

In other embodiments, the instrument further includes a sample chamber and a second light focusing element, the first light focusing element that includes a fiber optic having a first end disposed in the sample chamber, the second light focusing element being focused on the first end of the fiber optic. In another embodiment, the sample chamber includes a flow chamber.

In some embodiments, the instrument further includes an emission filter positioned to receive light transmitted through the second light focusing element and to transmit the light to the detector. In one embodiment, the light focusing element includes a first fiber optic coupled to the excitation source, and the instrument further includes a second fiber optic positioned to receive light emitted by a sample excited by the excitation source. In another embodiment, the second fiber optic is in a perpendicular relationship to the first fiber optic. In one embodiment, the second fiber optic is in a linear relationship with the first fiber optic.

In other embodiments, the instrument further includes a second light focusing element, the first light focusing element being in a perpendicular relationship to the second light focusing element. In another embodiment, the instrument further includes a second light focusing element, the first light focusing element being in a linear relationship with the second light focusing element.

In some embodiments, the instrument further includes an emission filter positioned to receive light from a second fiber optic and to transmit light to the detector. In other embodiments, the instrument further includes an emission filter positioned to receive light from the aperture and to transmit light to the detector. In another embodiment, the instrument further includes a third fiber optic positioned to transmit light from the emission filter to the detector.

In one embodiment, the light focusing element includes a first fiber optic coupled to the excitation source, and the instrument further includes a sample chamber, an end of the first fiber optic extending into the sample chamber, a second light focusing element, and an emission filter positioned to receive light from the second light focusing element and to transmit light to the detector. In some embodiments, the second light focusing element is focused on the end of the fiber optic. In other embodiments, the second light focusing element includes a lens.

In other embodiments, the instrument further includes a first dichromatic mirror positioned to receive light from the excitation source, a second light focusing element positioned to receive light reflected from the dichromatic mirror, a first aperture, a third light focusing element positioned to receive light transmitted through the dichromatic mirror and through the first aperture, and a second dichromatic mirror positioned to receive light transmitted through the third light focusing element, the first detector being positioned to receive at least one of light reflected from the second dichromatic mirror and light transmitted through the dichromatic mirror.

In one embodiment, the instrument further includes a first emission filter positioned to receive at least one of light reflected from the second dichromatic mirror and light transmitted through the dichromatic mirror.

In some embodiments, the instrument further includes a second emission filter positioned to receive light transmitted through the second dichromatic mirror, the first emission filter positioned to receive light reflected by the dichromatic mirror, and a second detector positioned to receive light transmitted through the second emission filter.

In other embodiments, the instrument further includes a first reflective mirror positioned to receive light reflected from the first dichromatic mirror and to transmit the light to the second light focusing element. In one embodiment, the instrument further includes a first reflective mirror positioned to receive light reflected from the first dichromatic mirror and to transmit the light to the second light focusing element.

In some embodiments, the instrument further includes a fourth light focusing element positioned to receive light transmitted by the first dichromatic mirror and to focus the light on the first aperture.

In another embodiment, the second light focusing element is an infinity corrected objective and the fourth light focusing element includes a tube lens.

In some embodiments, the instrument further includes a first dichromatic mirror positioned to receive light from the excitation source, a second light focusing element positioned to receive light reflected by the first dichromatic mirror, a third light focusing element positioned to receive light transmitted through the dichromatic mirror, a second dichromatic mirror positioned to receive light passing through the third light focusing element, a first component that includes at least one of a first aperture and a first fiber optic, and a first detector positioned to receive at least one of light reflected from the second dichromatic mirror through the first component and light transmitted through the second dichromatic mirror through the first component. In one embodiment, the first component is a first aperture. In another embodiment, the first detector is positioned to receive light reflected from the second dichromatic mirror through the first component, and the instrument further includes a second component that includes at least one of a second aperture and a second fiber optic, and a second detector positioned to receive light transmitted through the second dichromatic mirror and through the second component.

In one embodiment, the first component is a first aperture and the second component is a second aperture. In another embodiment, the first component is a first fiber optic and the second component is a second fiber optic.

In other embodiments, the instrument further includes a first emission filter positioned to receive light reflected from the second dichromatic mirror.

In some embodiments, the instrument further includes a first emission filter positioned to receive light reflected from the second dichromatic mirror, and a second emission filter positioned to receive light transmitted through the second dichromatic mirror. In one embodiment, the first component includes a first fiber optic positioned to receive light transmitted through the first emission filter and to transmit the light to the first detector.

In other embodiments, the instrument further includes a second fiber optic positioned to receive light passing through the second emission filter and to transmit the light to the second detector.

In other embodiments, the instrument further includes a reflective mirror positioned to receive light reflected from the first dichromatic mirror and to transmit the light to the second light focusing element.

In some embodiments, the instrument further includes a first dichromatic mirror positioned to receive light emitted by the excitation source, a second light focusing element positioned to receive light reflected by the first dichromatic mirror, and a first emission filter positioned to receive light transmitted through the first dichromatic mirror and to transmit light to the detector.

In other embodiments, the instrument further includes a fiber optic positioned to receive light from the first emission filter and to transmit light to the detector.

In other embodiments, the instrument further includes an aperture positioned to receive light from the first emission filter and to transmit light to the detector.

In other embodiments, the instrument further includes a first reflective mirror positioned to receive light reflected by the first dichromatic mirror and to reflect the light to the second light focusing element.

In some embodiments, the instrument further includes a first fiber optic positioned to receive light emitted by a sample excited by the excitation source, a beam splitter positioned to receive light from the first fiber optic, a third fiber optic coupled to the beam splitter, a first emission filter positioned to receive light from the third fiber optic, a fourth fiber optic coupled to the beam splitter, a second emission filter positioned to receive light from the fourth fiber optic, and a second detector positioned to receive light from the second emission filter, the first detector being positioned to receive light from the first emission filter.

In one embodiment, the instrument further includes a fifth fiber optic positioned to receive light from the first emission filter and to transmit the light to the first detector.

In another embodiment, the instrument further includes a sixth fiber optic positioned to receive light from the second emission filter and to transmit the light to the second detector.

In some embodiments, the first fiber optic is in a perpendicular relationship to the first light focusing element.

In other embodiments, the first fiber optic is in a linear relationship with the first light focusing element. In one embodiment, the excitation source is a laser. In other embodiments, the excitation source is a multi-line laser.

In some embodiments, the instrument further includes a sample chamber. In one embodiment the sample chamber includes a flow chamber.

In other embodiments, the instrument further includes an excitation light attenuation device. In one embodiment the excitation light attenuation device includes a neutral density filter, a shutter, an acousto-optical coupler, a pockels cell, or a combination thereof.

In another embodiment, the portable fluorescence correlation spectroscopy instrument includes, a monochromatic light source, a light focusing device adapted to focus light emitted by the monochromatic light source on a sample, a detector capable of detecting light, a fiber optic positioned to receive light emitted by a sample excited by the light source, the fiber optic being coupled to the detector, and a correlator coupled to the detector, the correlator being capable of processing data received at the detector and providing data that includes autocorrelation data, crosscorrelation data, or a combination thereof.

In another aspect, the invention features an article that includes a carrying case, and a portable fluorescence correlation spectroscopy instrument described herein disposed in the carrying case.

In other aspects, the invention features a method of using a portable fluorescence correlation spectroscopy instrument described herein, said method comprising exciting a sample that includes a fluorophore. In one embodiment, the method further includes detecting the excitation and optionally analyzing the excitation.

The invention features a portable fluorescence correlation spectroscopy instrument. The FCS instrument can be constructed to be small, compact and light weight relative to existing FCS instruments such that it can fit in a carrying case, and can be transported in a manner similar to that of a carrying case. The FCS instrument can be operated in a fixed stage mode such that the focus is set to a fixed plane in the sample volume. The FCS can be configured to provide an FCS instrument capable of relatively simple operation and with relatively minimal user adjustment and alignment.

Other features and advantages will be apparent from the following description of the preferred embodiments and from the claims taken in conjunction with the accompanying drawings, in which identical reference numerals identify similar elements.

GLOSSARY

In reference to the invention, these terms have the meanings set forth below:

The term "fiber optic" refers to at least one fiber capable of carrying light.

The term "multi-mode fiber optic" refers to at least one fiber capable of carrying multiple wavelengths of light.

The term "single mode fiber optic" refers at least one fiber capable of carrying a single wavelength of light.

The term "light focusing element" refers to an element that constricts light to a relatively smaller volume.

BRIEF DESCRIPTION OF THE DRAWINGS

FIG. 3 is a side view schematic of the mirror and objective lens of the schematic diagram of FIG. 2.

FIG. 10 is a schematic of a fifth alternate embodiment of a fluorescence correlation spectroscopy instrument.

FIG. 11 is a schematic of an alternate embodiment the positioning of a sample chamber between the two pinhole-sized apertures of FIG. 10.

FIG. 12 is a schematic of a sixth alternate embodiment of a fluorescence correlation spectroscopy instrument.

FIGS. 15, 16, and 17a are front side views of various embodiments of flow chambers.

FIG. 17B is a left side view of the flow chamber of FIG. 17a rotated 90 degrees.

FIG. 18 is a schematic of a ninth alternate embodiment of a fluorescence correlation spectroscopy instrument.

FIG. 19 is a schematic of an alternate embodiment of the sample flow chamber of FIG. 18 positioned between two apertures.

DETAILED DESCRIPTION

Figure 1:
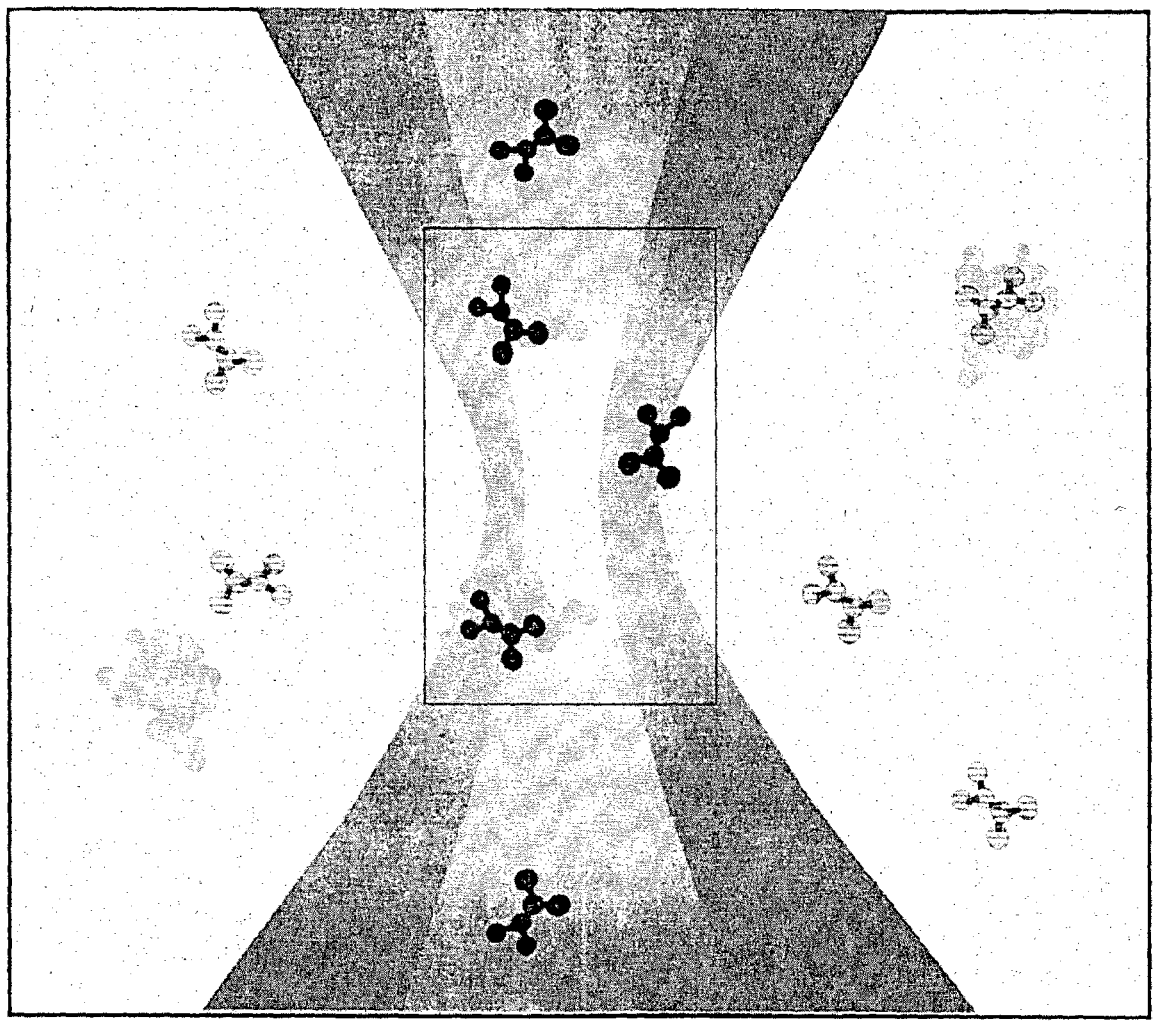
FIG. 1 illustrates the waist of a laser beam focused on a liquid sample volume that includes fluorescence-labeled particles.

FIGS. 2-5 illustrate a FCS instrument 2 that includes a DPSS laser 10, a light focusing lens 12 positioned on an x-y micrometer positioner, a neutral density filter 14, a dichromatic mirror 16, a 100% reflecting mirror 18, a primary objective lens 20, a pinhole-sized aperture 22 positioned on an x-y micrometer positioner, a secondary objective lens 26 mounted on an x-y micrometer positioner 25, a second dichromatic mirror 28, an first emission filter 30, a second emission filter 32, two multi-mode fiber optics 38, 36 each connected to the emission filter via a connector 34a, 34b (e.g., any suitable fiber optic connector including, e.g., FC connectors and SMA connectors) and coupled to an x-y-z micrometer positioner 27a, 27b, and a detector 40. In operation, the DPSS laser 10 emits monochromatic light having a wavelength of 532 nm. The 532 nm light is transmitted to the focusing lens 12, which expands the laser beam so that the light fills the back focal plane of the objective lens 20. Prior to arriving at the objective lens, the light passes through a neutral density filter 14, which attenuates the light to achieve a desired amount of light reaching the sample (not shown); the sample being positioned in the focal plane of the objective lens 20. Before reaching the objective lens 20, the attenuated light then passes to the first dichromatic mirror 16, which has the property of being able to transmit and reflect light of different wavelength. The properties of the dichromatic mirror 16 are selected such that the mirror reflects 98% of the 532 nm light coming from the laser and transmits from 90% to 100% of the light that is emitted from the sample in the form of fluorescence, i.e., light having a wavelength greater than 553 nm. The reflected light having a wavelength of 532 nm is then transmitted to the 100% reflective mirror 18, which is mounted at a 45° angle to the plane of the path of the in coming light. The mirror 18 reflects the light to the primary objective lens 20. One hundred percent of the light transmitted to the mirror 18 is reflected to the primary objective lens 20. The light fills the back focal plane of the objective lens forming a small focused beam on a sample positioned at the objective lens 20. In this arrangement, the objective lens 20 has a fixed tube length of 160 mm.

To the extent that a sample (not shown) positioned at the objective lens 20 and in the confocal volume emits fluorescence, the emitted fluorescence travels back down through the objective lens 20 to the mounted mirror 18. The mounted mirror 18 reflects 100% of the fluorescence back along the optical path to the first dichromatic mirror 16. The fluorescence emitted that has a wavelength greater than 553 nm is transmitted through the dichromatic mirror 16 and focused through a pinhole-sized aperture 22 spaced a distance of 160 mm away from the shoulder of the primary objective lens 20.

The fluorescence then passes to the secondary objective lens 26, which is in the optical path and is focused on the pinhole-sized aperture 22 (i.e., the image plane). The fluorescence passes through the secondary objective lens 26, to the second dichromatic mirror 28, which is mounted at a 45° angle to the optical path. The dichromatic mirror 28 reflects fluorescence having a wavelength less than 620 nm and transmits fluorescence having a wavelength greater than 620 nm. The fluorescence having a wavelength less than 620 nm travels to and through the emission filter 30. The emission filter 30 selects and transmits fluorescence having a wavelength from 575 nm to 615 nm. The transmitted fluorescence then enters the 1 mm diameter multi-mode fiber optic 36, which is maintained in position by an FC connector 34 and is mounted on an x-y-z micrometer positioner. The x-y-z micrometer positioner can ensure precise location of the focused image. The fluorescence is carried along the fiber optic 36 to a first photon detector 40a.

The fluorescence having a wavelength greater than 620 nm travels through the dichromatic mirror 28. The emission filter 32 selects and transmits fluorescence having a wavelength from 615 nm to 650 nm. The transmitted fluorescence then enters the 1 mm diameter multi-mode fiber optic 36, which is maintained in position by an FC connector 34 and is mounted on an x-y-z micrometer positioner. The fluorescence is carried along the fiber optic 38 to a second photon detector 40b. Output from the detectors 40a, 40b is sent to the digital hardware correlator where crosscorrelation and autocorrelation occurs. The data is then transferred to a computer via a USB cable The various components of the FCS instrument including, e.g., the lenses, fiber optics and pinhole-sized apertures, are arranged on x-y micrometer positioners 24 and include micrometer adjustment mechanisms to enable the components to be moved in two directions so as to align the optical path of the instrument. It is preferable to align the optical path of the instrument to obtain optimal results, data and data analysis.

Detectors 40a and 40b ouput positive TTL pulses that are sent to a hardware correlator via cables that are connected through a BNC connection. The correlator acquires and analyzes data received from the detectors 40a and 40b. A useful correlator is a FLEX2K 12×2 multiple tau external digital correlator available from Correlator.com, which has a theoretical sampling time of 12.5 nanoseconds, accepts two TTL inputs from a photomultiplier tube module via a BNC connector. Another suitable correlator is an ALV digital correlator from www.alvgmbh..de.

The FCS instrument includes data acquisition and data analysis software that can be run form a desktop or laptop computer with a USB port. The software analyzes data received from detectors 40a, 40b and displays the data on the computer screen with statistical parameters.

The FCS instrument can be utilized in an autocorrelation mode, a crosscorrelation mode, or a combination thereof. Autocorrelation measures the persistence of a single fluorescent particle in the confocal volume. Crosscorrelation measures the correlation between fluctuations in the fluorescence intensity at two wavelengths for two different fluorescent probes. The program in the correlator employs various algorithms to analyze and manipulate the data received from the detectors and to implement autocorrelation or crosscorrelation. These algorithms are based on the following relationships.

Autocorrelation temporally correlates fluorescence intensity fluctuations as labeled particles diffuse into and out of the detection volume. Statistical analysis of fluorescence intensity fluctuations results in an autocorrelation curve, which shows the decay of temporal correlation in fluorescence intensity over time. The autocorrelation function is given by:

$$G(\tau) = 1 + \frac{<\delta I(t) * \delta I(t+\tau)>}{<I>^2}, \quad (1)$$

where the $\delta I$'s refer to the deviations of the intensity about the mean $<I>$.

Crosscorrelation extends standard autocorrelation FCS by introducing two different fluorescent labels with distinct excitation and emission properties that can be detected in the same confocal volume. It temporally correlates the intensity fluctuations of two distinguishable labels. Coincidence of these fluorescent labels on the same macromolecule is detected as a change in amplitude, R, at short time points, $\tau$, and the amplitude of the crosscorrelation function is directly proportional to the concentration of dual-labeled fluorescent particles. The crosscorrelation function is given by:

$$r(\tau) = \frac{<\delta I_i(t) * \delta I_j(t+\tau)>}{SD_i * SD_j} \quad (2)$$

The correlation function of Equation 2 is the form commonly used in statistics. The correlation function goes to 1 for perfect crosscorrelation and to 0 for no crosscorrelation. Instrumentally, it is simpler to define the crosscorrelation function in a manner analogous to equation 1 for the autocorrelation function.

$$R(\tau) = 1 + \frac{<\delta I_i(t) * \delta I_j(t+\tau)>}{<I_i> * <I_j>} \quad (3)$$

This form is simpler to calculate in real-time from an ongoing data stream and has the further advantage that when $I_i=I_j$, then $R(\tau)=G(\tau)$.

The relaxation time for correlation relates to stochastic processes of randomization such as diffusion, while the size of the intensity fluctuations relates to the number of molecules or particles involved in the stochastic process. Autocorrelation functions have been used to analyze these fluctuations, and yield information on diffusion coefficients, aggregation state chemical concentration, chemical reaction kinetics, and stoichiometry of macromolecules in solution as well as in the plasma membrane of living cells.

From the data generated by the FCS instrument a variety of additional information can be obtained including, e.g., the presence or absence of interaction between particles, particle diffusion times, the stoichiometry of particle interactions, the concentration of interacting particles and the kinetics of the interaction between particles.

Nonlinear regression is used to fit the data obtained to a three dimensional (3D) autocorrelation function for samples in solution. The 3D autocorrelation function corresponds to Equation 4.

$$G(\tau) = 1 + \left(\frac{1}{N}\right)\left(1 - T + T\exp\left(\frac{-\tau}{\tau_T}\right)\right)\left(\sum_i \frac{F_i}{(1 + \tau/\tau_{D_i})(1 + \tau/K^2\tau_{D_i})^{\frac{1}{2}}}\right) \quad (4)$$

Parameter estimates are calculated for particle number (N), triplet state fraction (T), triplet state correlation time ($\tau_T$), particle fraction ($F_i$) and diffusion time ($\tau_{Di}$) for diffusing particle species i. The structure parameter, $K^2$ where $K=\omega_2/\omega_1$ ($\omega_2$ and $\omega_1$ being the exp(-2) beam radii in the z and x directions respectively) is determined separately and held constant for each fit.

As indicated above, the photon counts, autocorrelation and crosscorelation data from channels 36 and 38 are transferred to a computer via a USB port. The USB port serves as the interface to transfer data from the hardware correlator to the computer. The computer programs written to acquire and analyze autocorrelation and crosscorrelation data are dependent on the operating system of the computer.

The FCS instrument can be constructed to fit within a carrying case 43 and can be coupled to a suitable power source including a portable power source, e.g. a battery.

Figure 6:
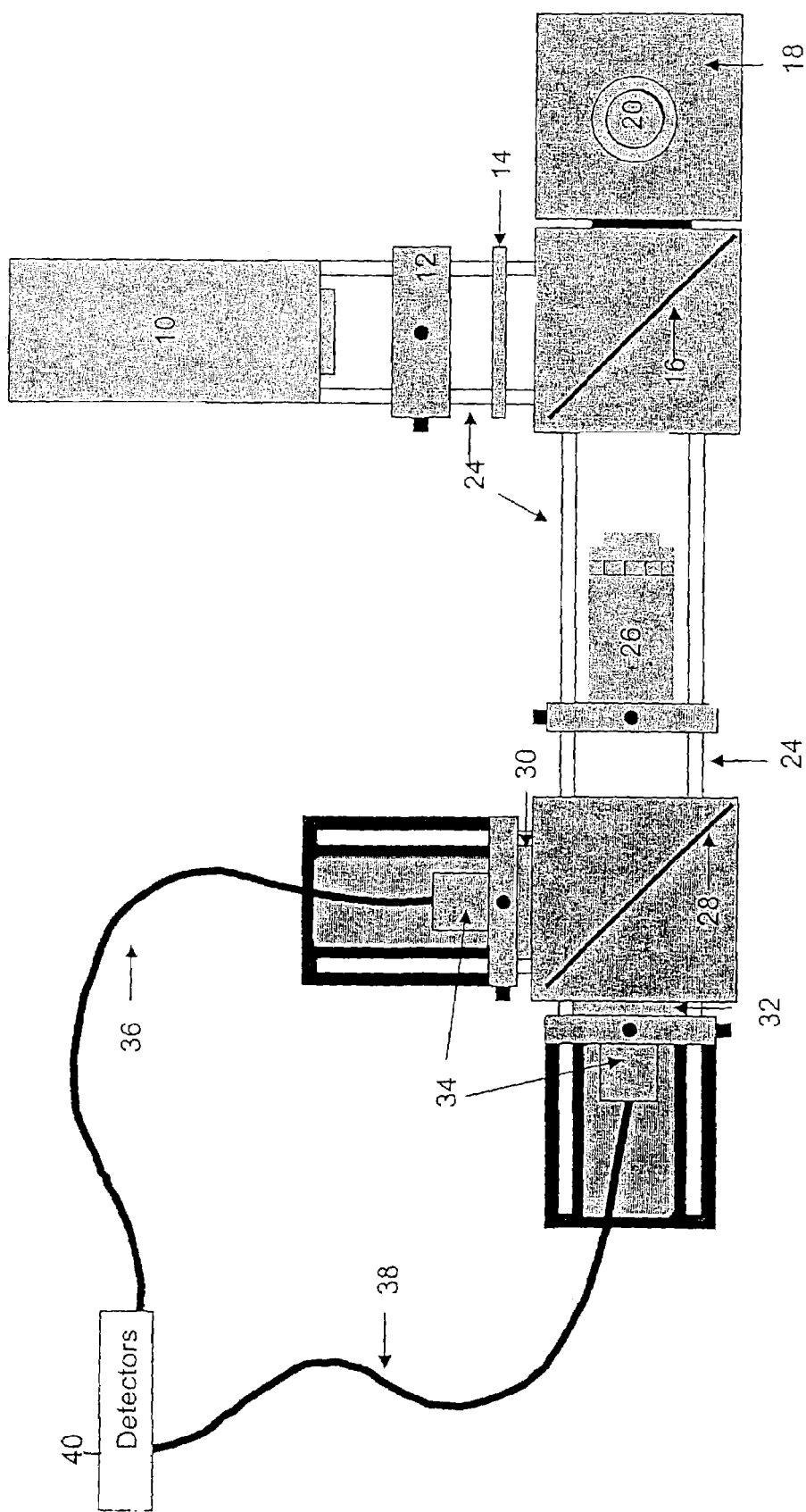
FIG. 6 is a schematic of a first alternate embodiment of a fluorescence correlation spectroscopy instrument.

Other embodiments are within the claims. FIG. 6, for example, illustrates another embodiment of a FCS instrument in which the pinhole-sized aperture 22 of FIG. 2 has been removed from its position in the FCS instrument of FIG. 2. In this configuration, an image is formed of the sample plane in the conjugate image plane and is precisely positioned in the area previously occupied by the pinhole-sized aperture 22 in FIG. 2. This enables the pinhole-sized aperture 22 to be removed and allows the objective lens 26 to be focused on the image plane. The confocal volume can be slightly larger relative to the confocal volume of the FCS instrument of FIG. 2 because more stray light in the z-axis focal plane will be imaged onto to the fiber optics 34 leading to the detectors 40.

Figure 2:
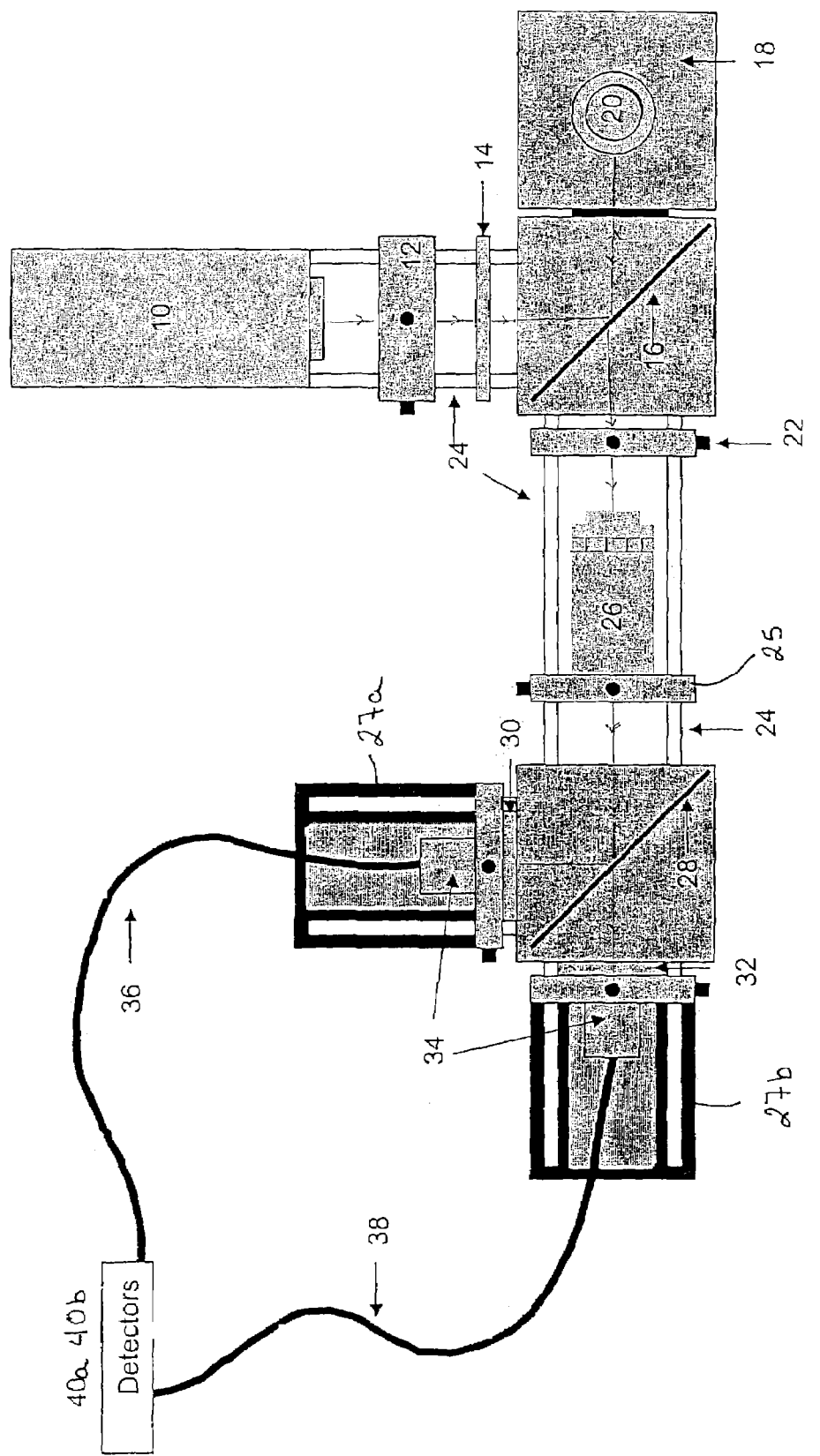
FIG. 2 is a schematic diagram of one embodiment of the fluorescence correlation spectroscopy instrument.
Figure 4:
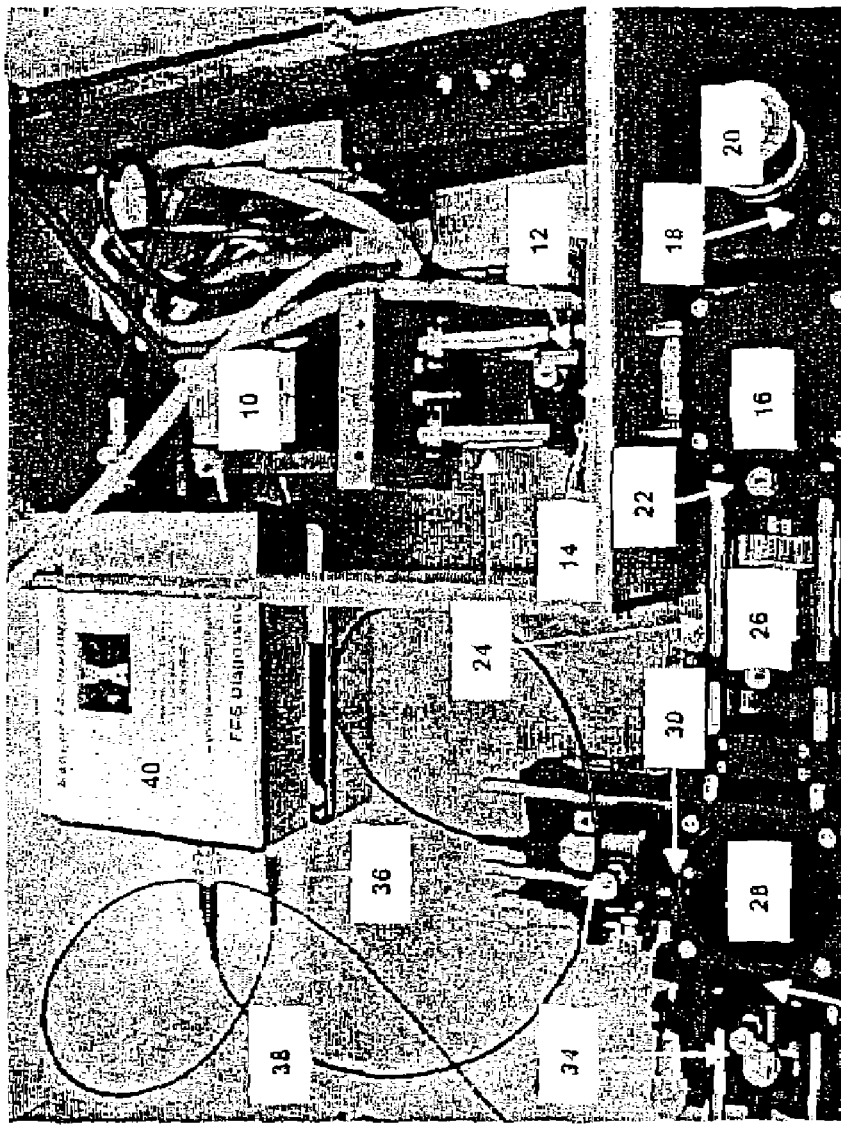
FIG. 4 is a photograph of a perspective view of fluorescence correlation spectroscopy instrument taken from above the instrument.
Figure 5:
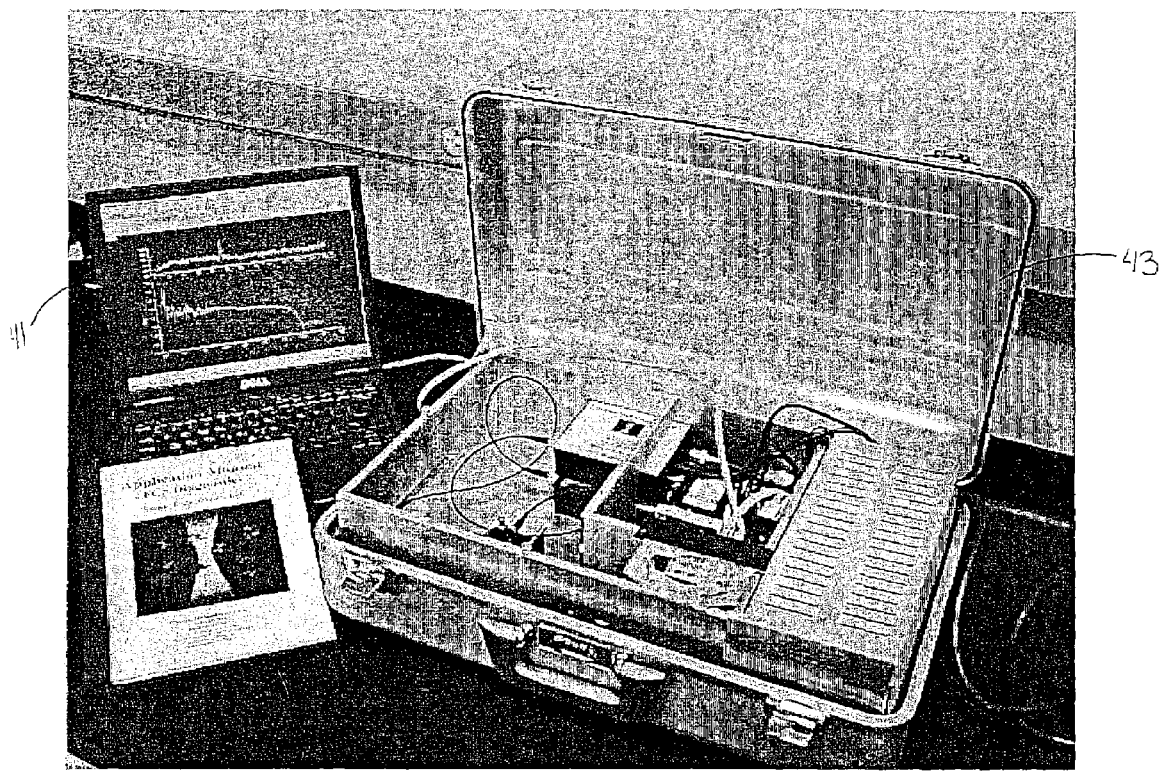
FIG. 5 is a photograph of the instrument of FIG. 4 disposed in a carrying case and operatively coupled to a lap top computer.
Figure 7:
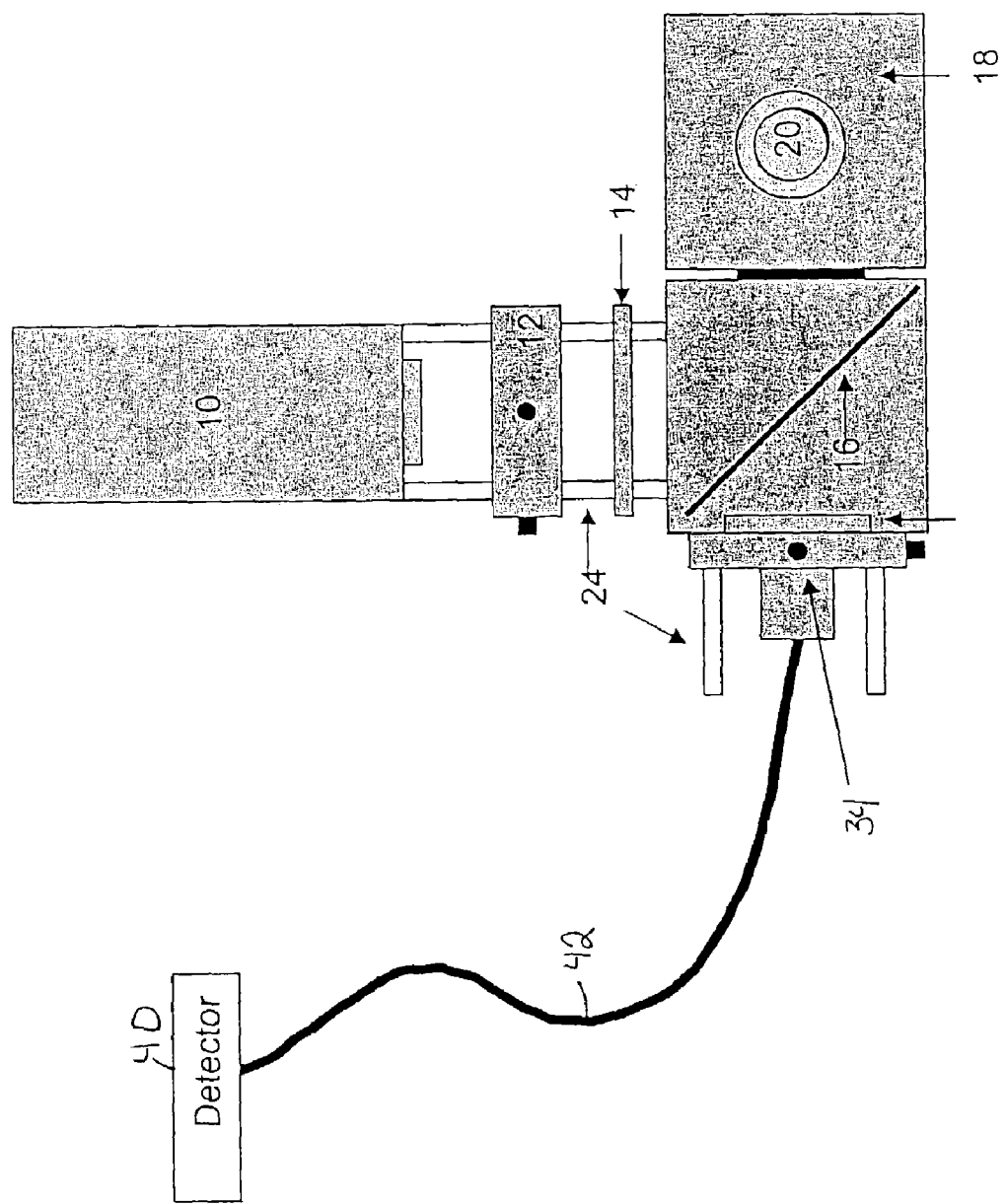
FIG. 7 is a schematic of a second alternate embodiment of a fluorescence correlation spectroscopy instrument.

FIG. 7 illustrates an embodiment of an FCS instrument in which the FCS instrument is configured to include a fiber optic 42 maintained in positioned in the area previously occupied by the pinhole-sized aperture 22 of FIG. 2 by a FC connector 34. Such a configuration enables the FCS instrument to function in an autocorrelation mode. The fiber optic 42 serves as the pinhole-sized aperture and carries the fluorescence signal to a single detector 40.

In another embodiment, the FCS instrument of FIG. 2 includes an aspheric lens instead of the secondary objective lens 26. The aspheric lens is positioned in the place of the secondary objective lens 26. In the various FCS instruments described herein, the secondary objective lens can be replaced with an aspheric lens.

In other embodiments, the lens 12 of any one of the embodiments of the FCS instrument can be replaced with a two-lens beam expansion system or a negative achromatic doublet lens.

Figure 8:
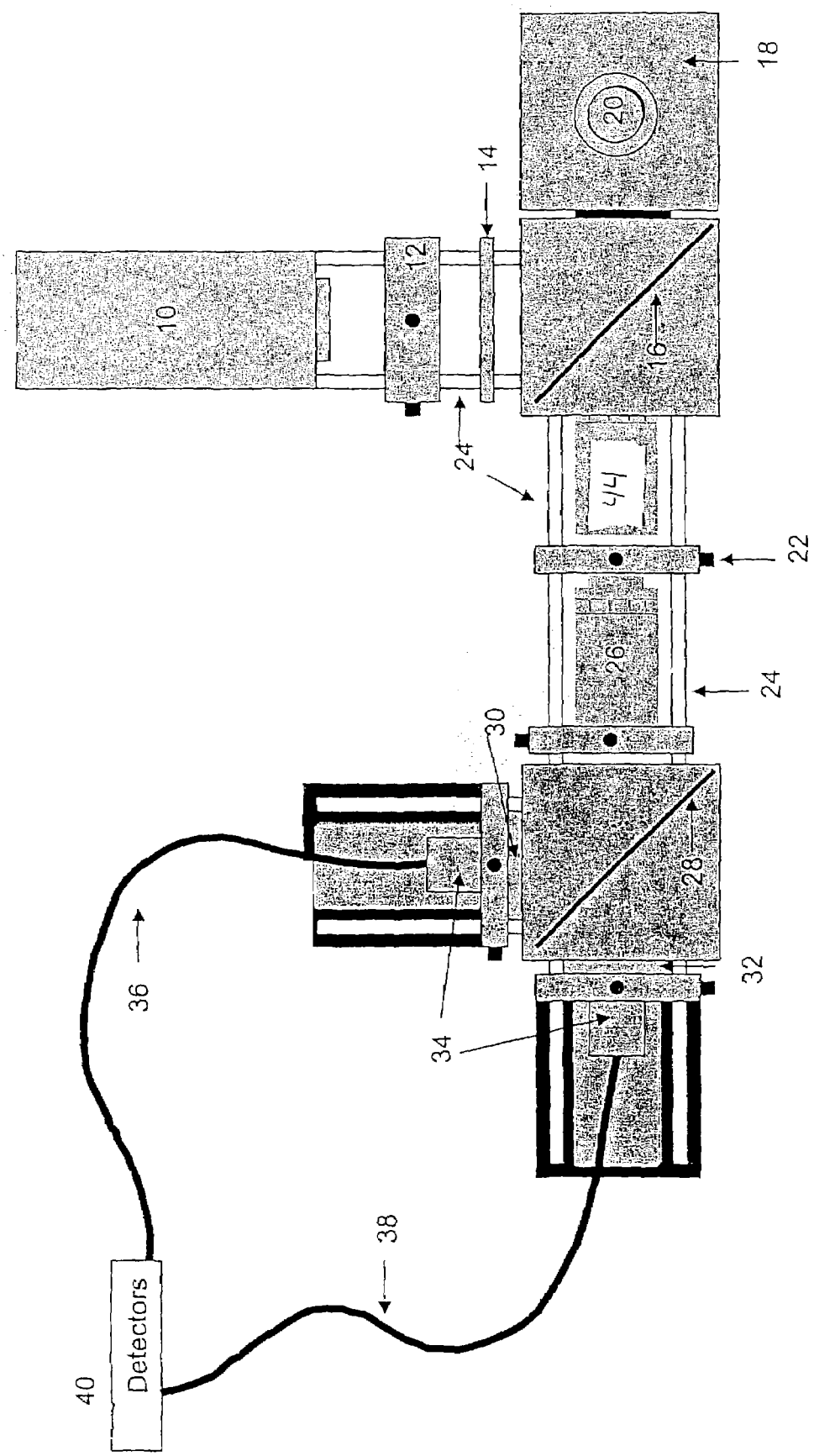
FIG. 8 is a schematic of a third alternate embodiment of a fluorescence correlation spectroscopy instrument.

FIG. 8 illustrates an FCS Instrument similar to that of FIG. 2 with the exception that the FCS instrument includes a tube lens 44 positioned in the optical path. The inclusion of a tube lens 44 in the instrument enables the implementation of infinity corrected optics. Infinity corrected optics eliminates certain size/distance constraints that exist in fixed tube length lens systems and enables the use of additional optics to achieve image focus in a desired location.

Figure 9:
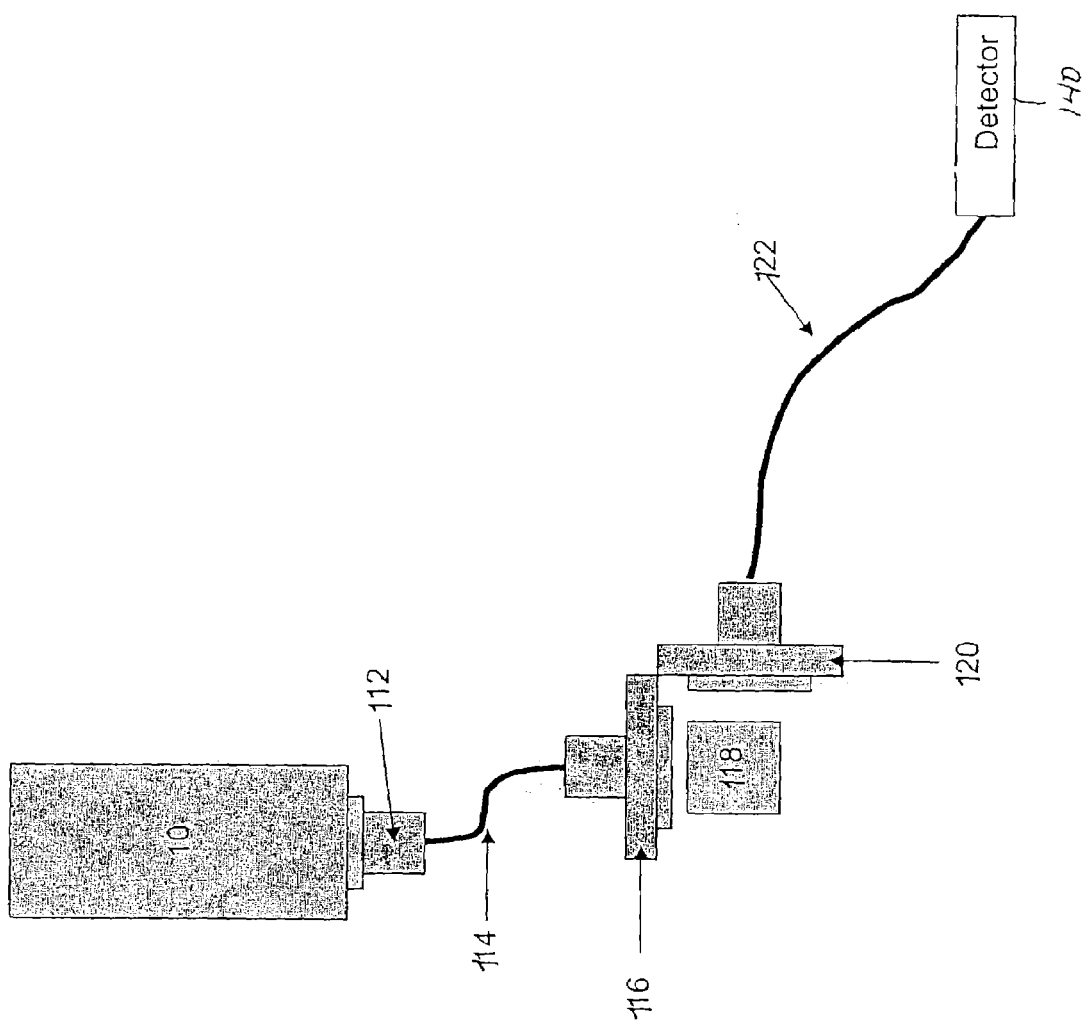
FIG. 9 is a schematic of a fourth alternate embodiment of a fluorescence correlation spectroscopy instrument.

FIG. 9 illustrates a lensless FCS instrument that includes two pinhole-sized apertures 116, 120 and no objective lenses. The first pinhole-sized aperture 116 is positioned between the laser 10 and the sample and the second pinhole-sized aperture 120 is positioned between the sample and the detector 140. The first pinhole-sized aperture 116 excludes stray light from the light source. The second pinhole-sized aperture 120 excludes stray fluorescence light emitted from the excited sample. The detector 140 is used to collect photons of emitted fluorescence from the sample after the emitted fluorescence passes through the aperture 120. Light from the laser 10 is transmitted to the sample 118 via a fiber optic 114. Fluorescence emitted by the sample due to excitation by the laser 10 is carried from the sample to the detector 140 via a fiber optic 122. The illumination 114 and detection fibers 122 are oriented at a 90° angle to each other. The sample chamber 118 in this case is a cuvette.

FIG. 10 illustrates a lensless FCS instrument in which the illumination 114 and detection fibers 122 are oriented in-line with each other rather than at a 90° angle to each other. The sample 118 is positioned between a first pinhole-sized aperture 116 and a second pinhole-sized aperture 120.

FIG. 11 illustrates a second embodiment of the FCS instrument illustrated in FIG. 10 in which the pinhole-sized apertures 116, 120 are positioned immediately adjacent the sample chamber 124 such that the sample chamber is sandwiched between the apertures 116, 120. The sample chamber 124 can be contained between the two pinhole-sized apertures 116, 120, or configured as a flow chamber as described below.

Alternatively, the apertures 116, 120 illustrated in FIGS. 9-11, can be removed and the fiber optic can serve as the pinhole-sized aperture. Alternatively, the FCS instrument can be configured to include any combination of an aperture and a fiber optic serving as the aperture.

FIG. 12 illustrates an FCS instrument that includes an additional chamber 130, which holds an emission filter 128 that is selective for the wavelength associated with the fluorescence emitted by the sample 118. The chamber 130 includes FC connections 125, 126 that couple fiber optics 122, 133 to the chamber 130. The emission filter 128 is positioned in the light path. The fiber optics 114, 122 are illustrated as being configured in a 90° orientation relative to each other. Alternatively, the fiber optics may be configured in line with each other. A third fiber optic 132 transmits the light to a detector 140.

Figure 13:
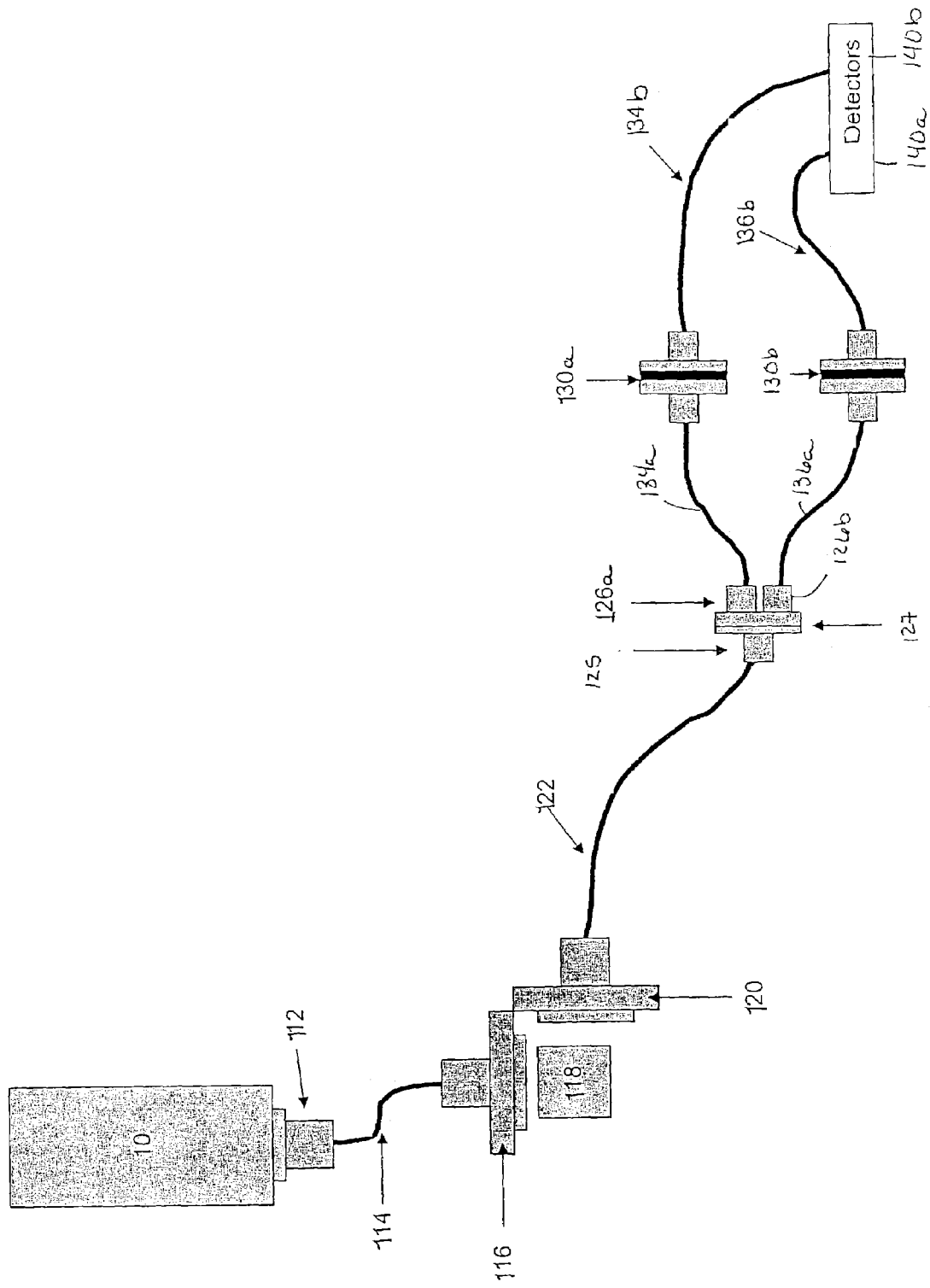
FIG. 13 is a schematic of an seventh alternate embodiment of a fluorescence correlation spectroscopy instrument.

FIG. 13 illustrates a modification of the lensless FCS instrument of FIG. 12. The FCS instrument includes a beam splitter 127 two emission filters 130*a*, 130*b* and two detectors 140a, 140b. The beam splitter 127 enables the use of the detector in a crosscorrelation mode. The two emission filters 130a, 130b are capable of selecting specific wavelengths of emitted fluorescence. The in line beam splitter 127 splits the fluorescence signal into two channels, each of which can be analyzed individually using autocorrelation techniques or together using crosscorrelation techniques. The two channels of light then separately pass to a first fiber optic 136a and a second fiber optic 134a, and then to the associated emission filters 130a, 130b, respectively. The emission filters selectively transmit light of a predetermined wavelength through the fiber optics 134b, 136b to the detectors 140a, 140b.

Figure 14:
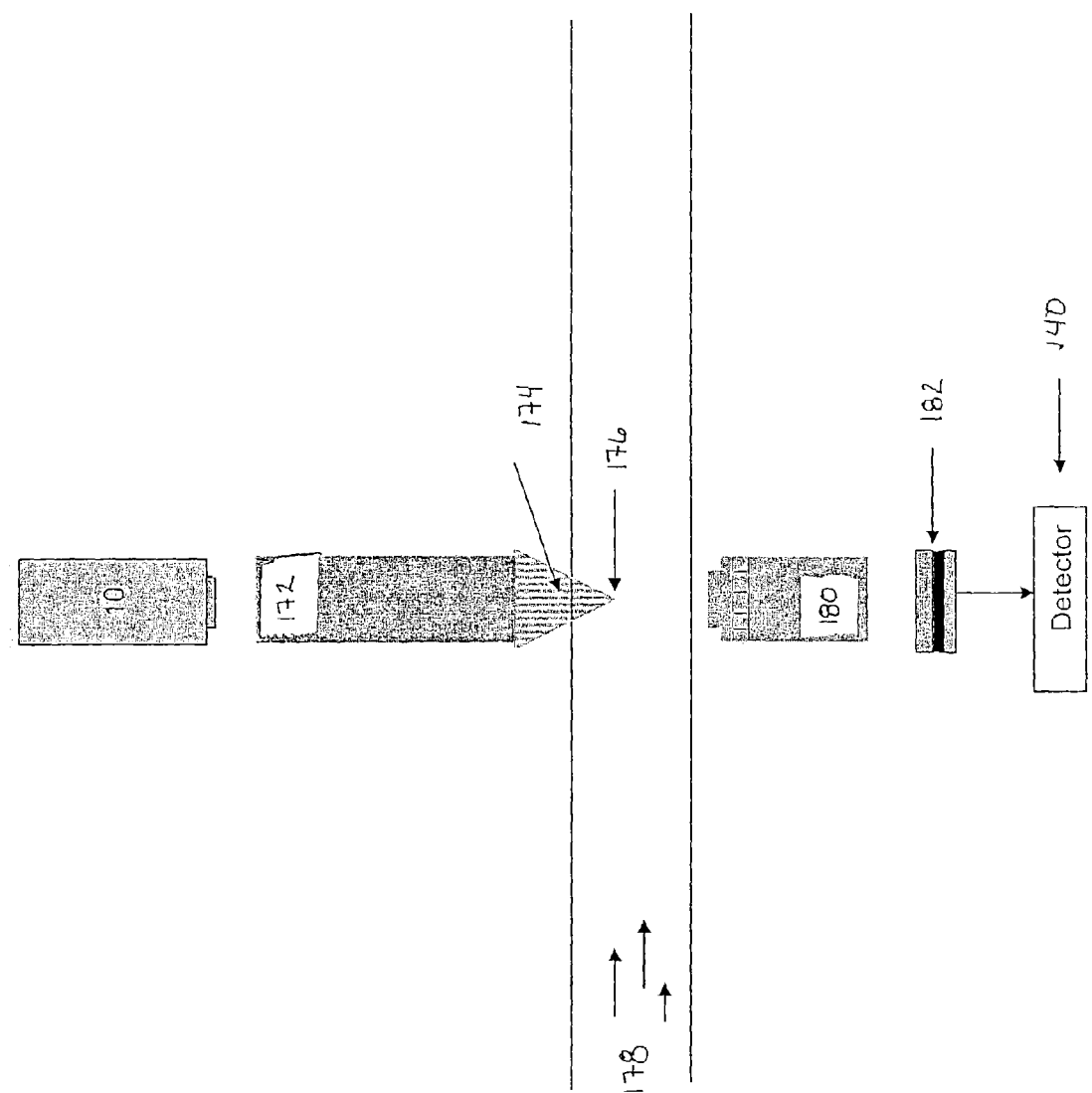
FIG. 14 is a schematic of a eighth alternate embodiment of a fluorescence correlation spectroscopy instrument.

Near-field optical scanning microscopy (NSOM) can be combined with FCS detection to obtain quantitative parameters provided by FCS analysis. FIG. 14 illustrates a generalized nearfield set-up. Light from a laser 10 is transmitted through a fiber optic 172 having a tapered end 174 that has an aluminized tip. The tip can be polished to have a suitable diameter, e.g., a diameter of no greater than 50 nm. The tip 176 functions as a probe 176 to illuminate the sample. An objective lens 180 is focused on the probe 176. A liquid sample 178 is passed through the focal plane of the microscope. As the solution passes by the probe, photons are collected through the microscope for FCS data analysis. The fluorescence emitted by the sample when excited by the laser light at the probe passes through the objective lens 180 and then through an emission filter 182 to the detector 140.

The sample can be positioned at the confocal volume by placing the sample in a sample chamber. The sample chamber can have a variety of configurations including, e.g., a single well and multiple wells. The sample chamber can include a control (e.g., to obtain baseline information), multiple samples, multiple controls, and combinations thereof. Useful chambers include optically clear cuvettes.

In another embodiment, the FCS instrument includes a flow chamber positioned in the confocal volume. The flow chamber includes a sample chamber dimensioned to receive a volume of sample, an input through which sample is brought into the sample chamber, and an output through which sample is passed out of the sample chamber. Tubing couples a sample reservoir to the input and the output to a waste receptacle. The tubing, input, sample chamber and output can be a continuous tube or can include multiple tubes and other components. Suitable flow chambers include, e.g., capillary tubing, cuvettes, cylindrical flow cells, and flat flow cells. FIGS. 15, 16, 17a and 17b illustrate various flow cell configurations including a cylindrical flow cell 150 and flat rectangular flow cells 152, 154 each of which includes inlet and outlet ports 156, 158.

Each of the FCS instrument configurations described herein can include a flow chamber or can be configured to utilize a flow chamber. The flow of sample through the chamber can be achieved with a pump, where the flow rate is greater than the diffusion time of the particles under study. In the case where the flow chamber is configured to function in a non-stochastic flow mode, information on particle number and coincidence of dual labeled particles can be obtained. This information can be used for crosscorrelation studies and coincidence analysis. Electrophoretic flow can also be implemented in the FCS instrument, in which case information about the relative electrophoretic-time constant of particles being studied can be obtained.

The system can also be configured to function in a pulsed flow mode. In this configuration, a flow chamber is implemented with pulsed movement of samples into and out of the observation volume. Pulsed flow can be achieved with a pump or using electrophoretic flow. In the pulsed flow mode, sample is pulsed into the observation volume, FCS detection occurs, and the sample is flowed out of the volume and replaced with new sample. In the pulsed flow mode, information about time constants can be obtained.

FIG. 18 illustrates one embodiment of a FCS instrument that includes a flow chamber 146 that includes an input coupled to an input tube 142 and an output coupled to an output tube 144. Sample flows through the input tubing 142 into the sample chamber 146 and out through the output tubing 144. The flow chamber 146 can be used as configured in FIGS. 14, or can be used at 90° angles as described in FIGS. 9, 12 and 13. Flow chambers can also be combined with crosscorrelation as configured in FIG. 13.

FIG. 19 illustrates an alternative configuration of the sample area of FIG. 15 in which the flow chamber is disposed between two pinhole-sized apertures 116, 120. Sample can be provided to the chamber through inlet tube 142 and removed from the chamber through outlet tube 144.

The invention has been described with respect to a laser emitting monochromtic light having a wavelength of 532 nm. The laser can be selected to emit any desired excitation wavelength. Available wavelengths will depend on the type of laser selected. Suitable lasers include ion lasers including, e.g., argon and argon/krypton lasers, produce multiple laser lines in wavelengths from about 457 nm to 568 nm. Ion lasers can be single-line, tunable multi-line, or simultaneous multi-line. An appropriate power level is selected. Suitable power levels include, e.g., about 1 mW, at least about 2 mW, about 5 mW, at least 20 mW, from 20 mW to 30 mW, from 1 mW to 10 W, or even from 30 mW to 10 W. If single wavelengths are to be used, helium-neon (HeNe) lasers emit light having a wavelength at either 543 nm or 635 nm. Other suitable lasers include solid-state diode lasers. Commercially available solid-state diode lasers are capable of emitting light having wavelengths from ultraviolet (UV) through infrared (IR) including, e.g., visible laser lines at wavelengths of 430 nm, 473 nm, 488 nm, 490 nm, 532 nm, 633 nm and 658 nm, at a variety of power levels including, e.g., from a few milliwatts (mW) to tens of mW. The selected laser preferably exhibits sufficient stability for the FCS application, preferably less than 3% peak to peak noise.

The instrument has been described with a laser as a light source. Another suitable light source is a light emitting diode (LED). The LED can be used as a continuous wave light source or as a pulsed light source.

Suitable fibers include polarization-maintaining fibers and wavelength-optimized single mode fibers (e.g. fibers optimized for 488 nm and/or 514 nm).

The selectively reflective, selectively transmissive mirrors can be selected based upon the desired wavelengths, both excitation and emission, utilized in the system including, e.g., the excitation and emission wavelengths of the fluorescence label(s) in the sample.

The data has been described as being displayed on a computer screen but could be sent to any suitable display including, e.g., laptop screens and chart recorders.

Other embodiments are within the claims.

What is claimed is:

1. A portable fluorescence correlation spectroscopy instrument comprising:
   a sample flow chamber;
   an excitation source;
   a first dichromatic mirror positioned to reflect light from said excitation source;

at least one light focusing element positioned to receive light emitted by said excitation source and transmitted through said first dichromatic mirror;

a detector for detecting light, said detector positioned to receive light emitted by a sample excited by said excitation source; and a correlator coupled to said detector, said correlator for processing data received at said detector and providing data comprising autocorrelation data, crosscorrelation data, or a combination thereof, the instrument being free of a microscope eyepiece.

2. The instrument of claim 1, further comprising an emission filter positioned to transmit light to said detector, said emission filter adapted to transmit light having a wavelength range greater than the range of wavelengths emitted by said excitation source.

3. The instrument of claim 1, wherein said light focusing element comprises a fiber optic.

4. The instrument of claim 3, wherein said fiber optic is coupled to said excitation source.

5. The instrument of claim 1, further comprising an aperture positioned to receive light emitted by a sample excited by said excitation source.

6. The instrument of claim 5 further comprising an emission filter positioned to receive light from said aperture and to transmit light to said detector.

7. The instrument of claim 6 further comprising a third fiber optic positioned to transmit light from said emission filter to said detector.

8. The instrument of claim 1, wherein said light focusing element comprises a focusing lens.

9. The instrument of claim 1, further comprising a second light focusing element positioned to focus light emitted by said excitation source in a sample volume.

10. The instrument of claim 9, further comprising a fiber optic coupled to said excitation source and said first light focusing element.

11. The instrument of claim 1, further comprising a second light focusing element, said first light focusing element comprising a fiber optic having a first end disposed in said sample chamber, said second light focusing element being focused on the first end of said fiber optic.

12. The instrument of claim 11 further comprising an emission filter positioned to receive light transmitted through said second light focusing element and to transmit said light to said detector.

13. The instrument of claim 1, wherein said light focusing element comprises a first fiber optic coupled to said excitation source, said instrument further comprising a second fiber optic positioned to receive light emitted by a sample excited by said excitation source.

14. The instrument of claim 13, wherein said second fiber optic is in a perpendicular relationship to said first fiber optic.

15. The instrument of claim 13, wherein said second fiber optic is in a linear axial relationship to said first fiber optic.

16. The instrument of claim 13 further comprising an emission filter positioned to receive light from said second fiber optic and to transmit light to said detector.

17. The instrument of claim 1 further comprising a second light focusing element, said first light focusing element being in a perpendicular relationship to said second light focusing element.

18. The instrument of claim 1 further comprising a second light focusing element, said first light focusing element being in a linear axial relationship with said second light focusing element.

19. The instrument of claim 1 wherein said light focusing element comprises a first fiber optic coupled to said excitation source, an end of said first fiber optic extending into said sample chamber, said instrument further comprising:

a second light focusing element; and an emission filter positioned to receive light from said second light focusing element and to transmit light to said detector.

20. The instrument of claim 19, wherein said second light focusing element is focused on said end of said fiber optic.

21. The instrument of claim 19, wherein said second light focusing element comprises a lens.

22. The instrument of claim 19, further comprising a second fiber optic positioned to receive light from said emission filter and to transmit light to said detector.

23. The instrument of claim 1, further comprising
a second light focusing element positioned to receive light reflected from said dichromatic mirror;
a first aperture;
a third light focusing element positioned to receive light transmitted through said dichromatic mirror and through said first aperture; and
a second dichromatic mirror positioned to receive light transmitted through said third light focusing element, said first detector being positioned to receive at least one of light reflected from said second dichromatic mirror and light transmitted through said dichromatic mirror.

24. The instrument of claim 1, further comprising:
a second light focusing element positioned to receive light reflected by said first dichromatic mirror;
a third light focusing element positioned to receive light transmitted through said dichromatic mirror;
a second dichromatic mirror positioned to receive light passing through said third light focusing element;
a first component comprising at least one of a first aperture and a first fiber optic; and
a first detector positioned to receive at least one of light reflected from said second dichromatic mirror through said first component and light transmitted through said second dichromatic mirror through said first component.

25. The instrument of claim 1, further comprising:
a second light focusing element positioned to receive light reflected by said first dichromatic mirror; and
a first emission filter positioned to receive light transmitted through said first dichromatic mirror and to transmit light to said detector.

26. The instrument of claim 25 further comprising a fiber optic positioned to receive light from said first emission filter and to transmit light to said detector.

27. The instrument of claim 25 further comprising an aperture positioned to receive light from said first emission filter and to transmit light to said detector.

28. The instrument of claim 25 further comprising a first reflective mirror positioned to receive light reflected by said first dichromatic mirror and to reflect said light to said second light focusing element.

29. The instrument of claim 1, further comprising
a first fiber optic positioned to receive light emitted by a sample excited by said excitation source;
a beam splitter positioned to receive light from said first fiber optic;
a third fiber optic coupled to said beam splitter;

a first emission filter positioned to receive light from said third fiber optic;
a fourth fiber optic coupled to said beam splitter;
a second emission filter positioned to receive light from said fourth fiber optic; and
a second detector positioned to receive light from said second emission filter,
said first detector being positioned to receive light from said first emission filter.

30. The instrument of claim 1, wherein said excitation source is a laser.

31. The instrument of claim 1, wherein said excitation source is a multi-line laser.

32. The instrument of claim 1, further comprising an excitation light attenuation device.

33. The instrument of claim 32, wherein said excitation light attenuation device comprises a neutral density filter, a shutter, an acousto-optical coupler, a pockels cell, or a combination thereof.

34. A fluorescence correlation spectroscopy system comprising:
a carrying case, and
the portable fluorescence correlation spectroscopy instrument of claim 1 disposed in said carrying case.

35. The instrument of claim 1, wherein said excitation source comprises a diode pumped solid state laser.

36. The instrument of claim 1, wherein said excitation source exhibits less than 3% peak to peak noise.

37. The instrument of claim 1, wherein said excitation source emits light at a wavelength of at least one of 430 nm, 473 nm, 488 nm, 490 nm, and 532 nm.

38. The instrument of claim 1, wherein said excitation source emits light at a wavelength of from about 457 nm to 568 nm.

39. The instrument of claim 1, wherein said excitation source emits light at a wavelength of 532 nm and said instrument is free of a microscope eyepiece.

40. The instrument of claim 1, wherein the excitation source exhibits a power level of from about 1 mW to 10 mW.

41. The instrument of claim 1, wherein a focus of the instrument is set to a fixed plane in the flow chamber.

42. The instrument of claim 1, wherein the instrument operates in a fixed stage mode.

43. A system comprising a battery and the instrument of claim 1 coupled to the battery.

44. A portable fluorescence correlation spectroscopy instrument comprising:
a chamber through which a liquid sample can flow, said chamber being positioned such that the confocal plane of said instrument is contained within said chamber;
a monochromatic light source;
a light focusing device adapted to focus light emitted by said monochromatic light source on a sample;
a detector capable of detecting light;
a fiber optic positioned to receive light emitted by a sample excited by said light source, said fiber optic being coupled to said detector; and
a correlator coupled to said detector, said correlator being capable of processing data received at said detector and providing data comprising autocorrelation data, cross-correlation data, or a combination thereof.

45. A portable fluorescence correlation spectroscopy instrument comprising:
a sample chamber;
an excitation source;
a first light focusing element comprising a fiber optic positioned to receive light emitted by said excitation source;
a second light focusing element, said fiber optic having a first end disposed in said sample chamber, said second light focusing element being focused on the first end of said fiber optic;
a detector for detecting light, said detector positioned to receive light emitted by a sample excited by said excitation source; and
a correlator coupled to said detector, said correlator for processing data received at said detector and providing data comprising autocorrelation data, crosscorrelation data, or a combination thereof.

46. The instrument of claim 45 further comprising an emission filter positioned to transmit light to said detector, said emission filter adapted to transmit light having a wavelength range greater than the range of wavelengths emitted by said excitation source.

47. The instrument of claim 45, wherein said fiber optic is coupled to said excitation source.

48. The instrument of claim 45, wherein said second light focusing element comprises a second fiber optic in a perpendicular relationship to said fiber optic of said first light focusing element.

49. The instrument of claim 45, wherein said second light focusing element comprises a second fiber optic and said second fiber optic is in a linear axial relationship with said first fiber optic.

50. The instrument of claim 45, wherein said second light focusing element comprises a second fiber optic, said instrument further comprising an emission filter positioned to receive light from said second fiber optic and to transmit light to said detector.

51. The instrument of claim 50 further comprising a third fiber optic positioned to transmit light from said emission filter to said detector.

52. The instrument of claim 45, wherein said second light focusing element comprises a lens.

53. The instrument of claim 45 further comprising
a beam splitter positioned to receive light from said second light focusing element;
a second fiber optic coupled to said beam splitter;
a first emission filter positioned to receive light from said second fiber optic;
a third fiber optic coupled to said beam splitter;
a second emission filter positioned to receive light from said third fiber optic; and
a second detector positioned to receive light transmitted through said second emission filter,
said first detector being positioned to receive light transmitted through said first emission filter.

54. The instrument of claim 45, wherein said excitation source is at least one of a laser and a light emitting diode.

55. The instrument of claim 45, wherein said excitation source is a multi-line laser.

56. The instrument of claim 45, further comprising an excitation light attenuation device.

57. The instrument of claim 45, wherein said excitation light attenuation device comprises a neutral density filter, a shutter, an acousto-optical coupler, a pockels cell, or a combination thereof.

58. A fluorescence correlation spectroscopy system comprising:
a carrying case, and
the portable fluorescence correlation spectroscopy instrument of claim 45, disposed in said carrying case.

59. The instrument of claim 45, wherein said excitation source emits light at a wavelength of from about 457 nm to 568 nm.

60. The instrument of claim 45, wherein said excitation source comprises a diode pumped solid state laser.

61. The instrument of claim 45, wherein said excitation source exhibits less than 3% peak to peak noise.

62. The instrument of claim 45, wherein said excitation source emits at a wavelength of 430 nm, 473 nm, 488 nm, 490 nm, 532 nm, 543 nm or a combination thereof.

63. The instrument of claim 45, wherein the power level of said excitation source is from 1 mW to 10 mW.

64. The instrument of claim 45 further comprising a neutral density filter disposed between the excitation source and the sample flow chamber.

65. A fluorescence correlation spectroscopy system comprising:

a carrying case; and a portable fluorescence correlation spectroscopy instrument disposed in said carrying case and being operable in said carrying case, said instrument comprising a sample flow chamber, an excitation source, at least one light focusing element positioned to receive light emitted by said excitation source, a detector for detecting light, said detector positioned to receive light emitted by a sample excited by said excitation source, and a correlator coupled to said detector, said correlator for processing data received at said detector and providing data comprising autocorrelation data, crosscorrelation data, or a combination thereof.

66. A portable fluorescence correlation spectroscopy instrument comprising:

a sample flow chamber;

an excitation source;

at least one light focusing element positioned to receive light emitted by said excitation source;

a detector for detecting light, said detector positioned to receive light emitted by a sample excited by said excitation source;

an emission filter positioned to transmit light to said detector, said emission filter adapted to transmit light having a wavelength range greater than the range of wavelengths emitted by said excitation source; and a correlator coupled to said detector, said correlator for processing data received at said detector and providing data comprising autocorrelation data, crosscorrelation data, or a combination thereof, said instrument operating in a fixed stage mode.

* * * * *